United States Patent
Sumitani

(10) Patent No.: US 7,921,706 B2
(45) Date of Patent: Apr. 12, 2011

(54) NOX SENSOR DIAGNOSTIC DEVICE AND EXHAUST GAS PURIFYING SYSTEM USING THE DEVICE

(75) Inventor: Shinya Sumitani, Nagoya (JP)

(73) Assignee: Denso Corporation, Kariya (JP)

(*) Notice: Subject to any disclaimer, the term of this patent is extended or adjusted under 35 U.S.C. 154(b) by 164 days.

(21) Appl. No.: 12/349,631

(22) Filed: Jan. 7, 2009

(65) Prior Publication Data
US 2009/0173140 A1    Jul. 9, 2009

(30) Foreign Application Priority Data
Jan. 9, 2008 (JP) .................... 2008-002328

(51) Int. Cl.
*G01M 15/00* (2006.01)
(52) U.S. Cl. .............. 73/114.69; 73/23.31; 73/114.71
(58) Field of Classification Search ............ 73/23.31, 73/114.69, 114.71
See application file for complete search history.

(56) References Cited

U.S. PATENT DOCUMENTS

| 6,453,663 | B1* | 9/2002 | Orzel et al. ............ 60/277 |
| 6,843,240 | B1* | 1/2005 | Hahn et al. ............ 123/688 |
| 6,860,100 | B1* | 3/2005 | Bidner et al. .......... 60/277 |
| 7,581,390 | B2* | 9/2009 | Andrews et al. ........ 60/301 |
| 2004/0187482 | A1* | 9/2004 | Bidner et al. ........ 60/285 |
| 2009/0013666 | A1* | 1/2009 | Jung .................... 60/277 |
| 2009/0282808 | A1* | 11/2009 | Andrews et al. ...... 60/277 |
| 2010/0024520 | A1* | 2/2010 | Sawada et al. ........ 73/23.31 |
| 2010/0095933 | A1* | 4/2010 | Moriya et al. ........ 123/435 |

FOREIGN PATENT DOCUMENTS

| JP | 2002-047979 | 2/2002 |
| JP | 2003-120399 | 4/2003 |

* cited by examiner

*Primary Examiner* — Freddie Kirkland, III
(74) *Attorney, Agent, or Firm* — Nixon & Vanderhye P.C.

(57) ABSTRACT

A NOx sensor diagnostic device includes a NOx sensor disposed in an exhaust passage of an engine, an output value obtaining device for obtaining an output value of the NOx sensor, a spray characteristics changing device for changing spray characteristics for a specific cylinder of cylinders of the engine, and a diagnostic device for diagnosing abnormality of the NOx sensor, based on the output value of the NOx sensor that is changed as a result of the change of the spray characteristics for the specific cylinder by the spray characteristics changing device. An exhaust gas purifying system includes a NOx removal system disposed in an exhaust passage of an engine, a NOx sensor disposed in the exhaust passage at least on an upstream side of the NOx removal system in a flow direction of exhaust air flowing through the exhaust passage, and the NOx sensor diagnostic device.

7 Claims, 5 Drawing Sheets

NOX SENSOR DIAGNOSTIC DEVICE AND EXHAUST GAS PURIFYING SYSTEM USING THE DEVICE

CROSS REFERENCE TO RELATED APPLICATION

This application is based on and incorporates herein by reference Japanese Patent Application No. 2008-2328 filed on Jan. 9, 2008.

BACKGROUND OF THE INVENTION

1. Field of the Invention

The present invention relates to a NOx sensor diagnostic device that diagnoses abnormality of a NOx sensor disposed in an exhaust passage of an internal combustion engine, and an exhaust gas purifying system using the device.

2. Description of Related Art

An exhaust gas purifying system for detecting NOx concentration in an exhaust passage based on an output value of a NOx sensor disposed in the exhaust passage of an internal combustion engine is conventionally known (see, e.g., JP-A-2003-120399 and JP-A-2002-047979).

In such an exhaust gas purifying system, abnormality of the NOx sensor due to deterioration, failure or the like needs to be diagnosed in order to detect the NOx concentration with high precision. In JP-A-2003-120399, the concentration of NOx discharged into the exhaust passage is forcibly fluctuated by fluctuating displacement or temperature of exhaust air circulated in a combustion chamber, or ignition timing of fuel more greatly than normal control. If the resultant variation of the output value of the NOx sensor is shifted from a range that the output value can cover when the NOx sensor is normal, it is determined that the NOx sensor is abnormal.

In JP-A-2002-047979, abnormality of an exhaust emission control device including the NOx sensor is detected by determining whether the output value of the NOx sensor corresponds to the amount of NOx emission of 0 (zero), in an operational state in which an amount of NOx emission from an internal combustion engine is estimated to be 0 (zero) in a fuel-cut state, for example.

However, in JP-A-2003-120399, while the abnormality of the NOx sensor is being diagnosed, the displacement or temperature of exhaust air circulated in the combustion chamber, or the ignition timing of fuel is repeatedly changed more greatly than the normal control. As a result, the engine operation condition fluctuates more greatly than the normal control during the abnormality diagnosis of the NOx sensor.

By the method of diagnosing the abnormality of the NOx sensor by determining whether the output value of the NOx sensor corresponds to the amount of NOx emission of 0 (zero), in an operational state in which the amount of NOx emission from the engine is estimated to be 0 (zero), such as in JP-A-2002-047979, it is difficult to distinguish between normal and abnormality of the NOx sensor with high precision because the level of the output value is low even if the NOx sensor is normal.

SUMMARY OF THE INVENTION

The present invention addresses the above disadvantages. Thus, it is an objective of the present invention to provide a NOx sensor diagnostic device that diagnoses abnormality of a NOx sensor with high precision, with fluctuation of an engine operation condition due to the abnormality diagnosis reduced as far as possible, and an exhaust gas purifying system using the device.

To achieve the objective of the present invention, there is provided a NOx sensor diagnostic device for an internal combustion engine. The device includes a NOx sensor, an output value obtaining means, a spray characteristics changing means, and a diagnostic means. The NOx sensor is disposed in an exhaust passage of the engine. The output value obtaining means is for obtaining an output value of the NOx sensor. The spray characteristics changing means is for changing spray characteristics for a specific cylinder of a plurality of cylinders of the engine. The diagnostic means is for diagnosing abnormality of the NOx sensor, based on the output value of the NOx sensor that is changed as a result of the change of the spray characteristics for the specific cylinder by the spray characteristics changing means.

To achieve the objective of the present invention, there is also provided an exhaust gas purifying system for an internal combustion engine. The system includes a NOx removal system, a NOx sensor, and the NOx sensor diagnostic device. The NOx removal system is disposed in an exhaust passage of the engine. The NOx sensor is disposed in the exhaust passage at least on an upstream side of the NOx removal system in a flow direction of exhaust air flowing through the exhaust passage.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF THE INVENTION

Figure 1:
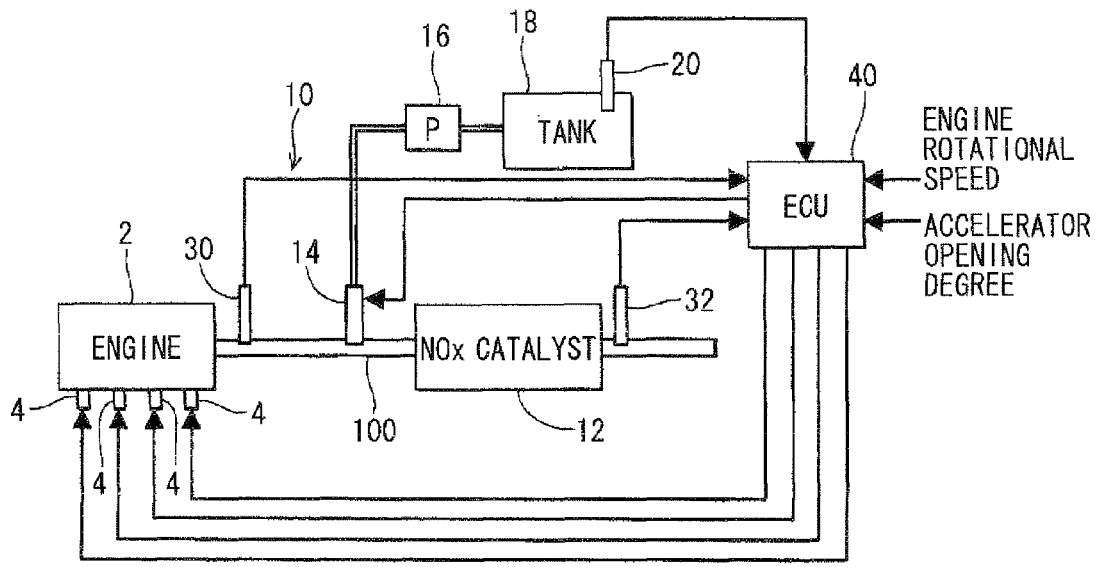
FIG. 1 is a block diagram illustrating an exhaust gas purifying system according to an embodiment of the invention.

Embodiments of the invention are described below with reference to the accompanying drawings. An exhaust gas purifying system according to an embodiment is shown in FIG. 1.

(Exhaust Gas Purifying System 10)

The exhaust gas purifying system 10 of the embodiment includes a NOx catalyst 12, a urea addition valve 14, a pump 16, a urea water tank 18, a level sensor 20, NOx sensors 30, 32, and an electronic control unit (ECU) 40. The exhaust gas purifying system 10 is a system that purifies exhaust air discharged into an exhaust passage 100 from a diesel engine (hereinafter referred to as an engine) 2 as an internal combustion engine. Fuel whose pressure is accumulated in a common rail is injected through a fuel injection valve 4 into each cylinder of the 4-cylinder engine 2.

The fuel injection valve 4 is a widely known electromagnetic valve, which controls opening/closing of a nozzle hole by a nozzle needle by electromagnetically controlling a communicating state between a control chamber which applies fuel pressure to the nozzle needle in an injection-cutoff direction, and a low-pressure side.

The NOx catalyst 12 is disposed in the exhaust passage 100. The urea addition valve 14 as an addition apparatus is disposed on an upstream side of the NOx catalyst 12. The NOx catalyst 12 and the urea addition valve 14 constitute "a NOx removal system".

The urea addition valve 14 is an electromagnetically-driven opening and closing valve, which injects urea water as a reducing agent into the upstream side of the NOx catalyst 12. The urea water injected through the urea addition valve 14 is adsorbed to the NOx catalyst 12. When exhaust temperature becomes equal to or higher than a predetermined temperature, the urea water is hydrolyzed to be decomposed into ammonia and carbon dioxide. Then, the ammonia generated through the hydrolysis reduces NOx in the NOx catalyst 12.

The pump 16 supplies urea water in the urea water tank 18 to the urea addition valve 14. The level sensor 20 detects a remaining amount of urea water in the urea water tank 18. The NOx sensors 30, 32 have the same configurations. The output values of the NOx sensors 30, 32 vary according to NOx concentration. The NOx sensor 30 is disposed on the upstream side of the NOx catalyst 12, and detects NOx concentration in exhaust air discharged from the engine 2. The NOx sensor 32 is disposed on a downstream side of the NOx catalyst 12, and detects NOx concentration in the exhaust air discharged from the NOx catalyst 12 without being reduced in the NOx catalyst 12.

An electronic control unit (ECU) 40 as a NOx sensor diagnostic device includes a central processing unit (CPU), a random access memory (RAM), a read-only memory (ROM), and a rewritable storage device such as a flash memory, which are not shown. The ECU 40 obtains an engine operation condition based on detection signals of various sensors including the NOx sensors 30, 32. The ECU 40 controls injection timing and injection quantity of the fuel injection valve, and behaviors of other devices, based on the obtained engine operation condition. The ECU 40 controls the injection timing, injection quantity, and injection pattern of the fuel injection valve 4 based on an injection pulse signal.

When a pulse width of the injection pulse signal is long, a period during which the control chamber of the fuel injection valve 4 is open to the low-pressure side is long. Therefore, the injection quantity increases. The ECU 40 stores a relationship between the injection pulse width and the injection quantity in the storage device for each common-rail pressure as a spray-characteristics map. The injection timing of the fuel injection valve 4 is determined by rising timing of the injection pulse signal.

The ECU 40 controls the injection pattern of the fuel injection valve 4 that performs multi-stage injection in one combustion cycle, using the number of steps of the injection pulse signal that commands the fuel injection valve 4 to inject fuel in one combustion cycle.

The ECU 40 stores a relationship between the output value of the NOx sensors 30, 32 and the NOx concentration, and a response time after changing the spray characteristics of the fuel injection valve 4 until the NOx sensors 30, 32 detect and output the change of the NOx concentration in accordance with the change of spray characteristics, in the storage device as initial output characteristics of the NOx sensors 30, 32. The ECU 40 obtains output values from the NOx sensors 30, 32, and obtains NOx concentration according to the output value based on the output characteristics of the NOx sensors 30, 32.

The ECU 40 performs abnormality diagnosis of the NOx sensors 30, 32 based on the obtained output values of the NOx sensors 30, 32. Abnormality diagnosis of the NOx sensor 32 disposed on the downstream side of the NOx catalyst 12 is performed only at a low temperature (i.e., exhaust gas temperature has not reached an active temperature, at which urea water is hydrolyzed to generate ammonia). The ECU 40 usually only performs abnormality diagnosis of the NOx sensor 30 disposed on the upstream side of the NOx catalyst 12. The abnormality diagnosis of the NOx sensor 30 disposed on the upstream side of the NOx catalyst 12 is described below.

The ECU 40 serves as the following means according to control programs stored in the storage devices, such as the ROM and flash memory of the ECU 40.

(Operational State Obtaining Means)

The ECU 40 obtains an engine operation condition from detection signals of the NOx sensors 30, 32, and various sensors such as an engine rotational speed sensor and accelerator opening degree sensor, which are not shown.

(Output Value Obtaining Means)

The ECU 40 obtains the output signal of the NOx sensor 30 as an output value. Based on the output value of the NOx sensor 30, the ECU 40 calculates NOx concentration in exhaust air on the upstream side of the NOx catalyst 12, and a response time for the NOx sensor 30 to detect and output the variation of the NOx concentration according to the change of the spray characteristics of the fuel injection valve 4 from the output characteristics of the NOx sensor 30.

(Spray Characteristics Changing Means)

When the abnormality diagnosis of the NOx sensor 30 is performed, the ECU 40 sets spray characteristics which are different from a target value calculated from the engine operation condition, not for all the cylinders but for a specific cylinder of four cylinders of the engine 2, and changes the spray characteristics. In the present embodiment, a cylinder #1 is described as a specific cylinder of the four cylinders. The specific cylinder of the four cylinders is not limited to the cylinder #1, and may be another cylinder.

Figure 2:
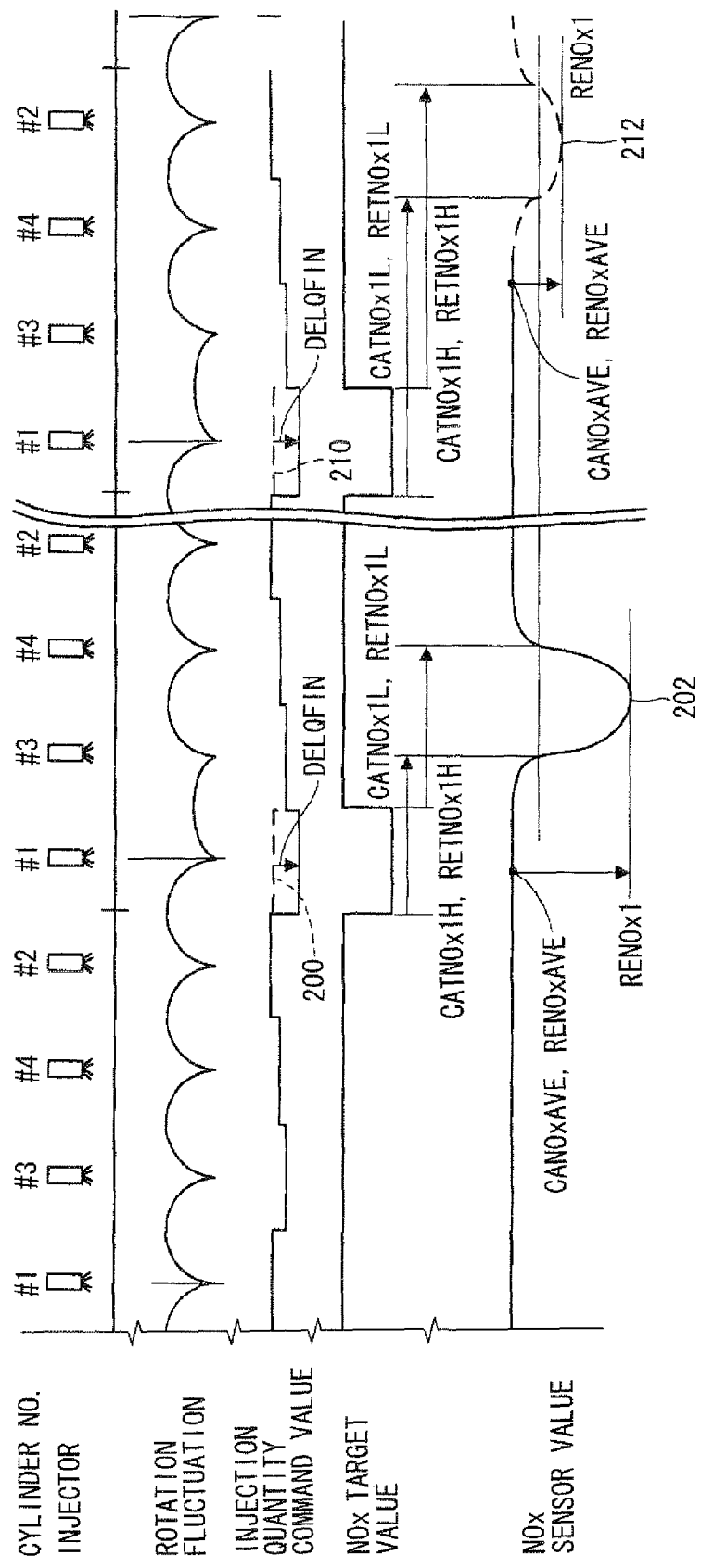
FIG. 2 is a timing diagram illustrating variation of a NOx value in accordance with change of spray characteristics of a specific cylinder according to the embodiment.

The ECU 40 changes the spray characteristics by varying change of injection timing of fuel injected into the specific cylinder due to an advance/retard angle or increase and decrease of the injection quantity, or the number of injection stages, an injection interval, which is a non-injection period between each injection in the multi-stage injection, or injection quantity of each injection in the multi-stage injection when multi-stage injection is carried out in one combustion cycle. For example, as shown in FIG. 2, the ECU 40 changes an injection quantity command value for the cylinder #1 by decreasing target injection quantity command values 200, 210 of the cylinder #1 calculated from the engine operation condition by a change injection quantity (DELQFIN). The ECU 40 calculates the change injection quantity (DELQFIN) based on the present engine rotational speed and fuel injection quantity. When the ECU 40 changes the fuel injection quantity for the cylinder #1, a combustion state of the engine 2 changes, and thereby the concentration of NOx discharged from the engine 2 changes.

In this manner, because spray characteristics for the specific cylinder #1 of the four cylinders are only changed, the combustion state changes only in the cylinder #1 in a combustion chamber of the engine 2 due to the change of spray characteristics. Accordingly, the change of the engine operation condition due to the change of spray characteristics is reduced as much as possible.

Spray characteristics are changed only in the specific cylinder #1 for the abnormality diagnosis of the NOx sensor 30. Accordingly, a relationship between the change of spray characteristics for the cylinder #1 and change characteristics of the output value of the NOx sensor 30 that varies according to the change of spray characteristics is clear. As a result, the abnormality of the NOx sensor 30 is diagnosed with high precision by a diagnostic means, which is described in greater detail hereinafter, based on the change of spray characteristics and the output value of the NOx sensor 30 that varies according to the change of spray characteristics.

The abnormality of the NOx sensor 30 is diagnosed based on the output value of the NOx sensor 30 that varies according to the change of spray characteristics for the specific cylinder #1. Accordingly, by appropriately setting a change amount of spray characteristics for the specific cylinder #1, the abnormality of the NOx sensor 30 is diagnosed with high precision through the diagnostic means, as compared to, for example, abnormality diagnosis based on the output value of the NOx sensor when the amount of NOx emission from the internal combustion engine is around 0 (zero).

(Diagnostic Means)

The ECU 40 diagnoses the abnormality of the NOx sensor 30 as described in the following (1) to (3) based on the output value of the NOx sensor 30 that varies when the spray characteristics changing means changes the spray characteristics for the specific cylinder of the four cylinders.

(1) Variation of the Output Value of the NOx Sensor 30

The ECU 40 diagnoses whether the NOx sensor 30 is abnormal based on a variation of the output value of NOx which changes due to the change of spray characteristics. For example, as described above, the ECU 40 changes the spray characteristics in the cylinder #1 by changing the injection quantity command value given to the fuel injection valve 4 for the cylinder #1 from the target injection quantity command value computed based on the engine operation condition. Then, the ECU 40 diagnoses whether the NOx sensor 30 is abnormal based on the resultant variation of the output value of NOx.

More specifically, the ECU 40 calculates the change injection quantity (DELQFIN), which is subtracted from the target injection quantity command values 200, 210 (see a dashed line in FIG. 2) of the injection quantity command value based on the engine operation condition in a regular stable state having a constant engine rotational speed, fuel injection quantity and the like. Instead of reducing the injection quantity command value from the target injection quantity command values 200, 210, a change injection quantity, which is added to the target injection quantity command values 200, 210, may be calculated. The regular stable state is, for example, an engine operation condition in which the fuel injection quantity and engine rotational speed do not change and are constant.

In a regular stable state, the ECU 40 calculates an average value (CANOxAVE) of NOx concentration as a NOx value discharged from the engine 2, and the concentration of NOx (CANOx1) discharged from the cylinder #1 as a result of decreasing the injection quantity command value for the cylinder #1 by the change injection quantity (DELQFIN), from the engine operation condition.

The ECU 40 detects an average value (RENOxAVE) of the concentration of NOx discharged from the engine 2 before changing the injection quantity command value from the target injection quantity command value by the change injection quantity (DELQFIN), and minimum valves (RENOx1) 202, 212 of the NOx concentration that has been reduced as a result of changing the injection quantity command value from the target injection quantity command value by the change injection quantity (DELQFIN), from the output value of the NOx sensor 30.

The ECU 40 diagnoses the NOx sensor 30 with normal, if a difference, which is a variation between the average value (RENOxAVE) of NOx concentration and the minimum valve (RENOx1) of NOx concentration detected from the output value of the NOx sensor 30, is within a predetermined range, as shown in a first period of FIG. 2. The predetermined range is calculated based on the average value (CANOxAVE) of NOx concentration and the NOx concentration (CANOx1) when the injection quantity command value is reduced by the change injection quantity (DELQFIN) calculated by the ECU 40.

The ECU 40 diagnoses the NOx sensor 30 with abnormal, when a difference between the average value (RENOxAVE) of NOx concentration and the minimum valve (RENOx1) of NOx concentration is shifted from the predetermined range, as shown in a latter half of FIG. 2.

(2) Response Time of the Output Value of the NOx Sensor 30

The ECU 40 diagnoses whether the NOx sensor 30 is abnormal based on a response time of the output value of NOx that varies according to the change of spray characteristics.

As described above, the ECU 40 first calculates the change injection quantity (DELQFIN), which is subtracted from the target injection quantity command values 200, 210 of the injection quantity command value based on the engine operation condition in a regular stable state having a constant engine rotational speed, fuel injection quantity and the like.

The ECU 40 calculates a decrease period (CATNOxIL) during which the output value of the NOx sensor 30 starts to decrease after starting an injection command to subtract the change injection quantity (DELQFIN) from the target injection quantity for the fuel injection valve 4 of the cylinder #1, and a recovery period (CATNOxIH), during which the change of the output value of the NOx sensor 30 is completed and then the output value starts to increase when the injection command to subtract the change injection quantity (DELQFIN) from the target injection quantity for the fuel injection valve 4 of the cylinder #1 is ended, and then the fuel injection valve 4 of a subsequent cylinder #3 starts to inject fuel, from the initial output characteristics associated with the response time of the NOx sensor 30.

The ECU 40 detects an actual decrease period (RETNOx1L) during which the output value of the NOx sensor 30 starts to decrease after starting the injection command to subtract the change injection quantity (DELQFIN) from the target injection quantity for the fuel injection valve 4 of the cylinder #1, and an actual recovery period (RETNOxIH) during which the change of the output value of the NOx sensor 30 is completed and then the output value starts to increase when the injection command to subtract the change injection quantity (DELQFIN) from the target injection quantity for the fuel injection valve 4 of the cylinder #1 is ended, and then the fuel injection valve 4 of a subsequent cylinder #3 starts to inject fuel, from the output value of the NOx sensor 30.

The ECU 40 diagnoses that the NOx sensor 30 is normal, if a difference between the recovery period (RETNOxIH) and the decrease period (RETNOx1L) of the output value of the NOx sensor 30 is within a predetermined range, as shown in a first period of FIG. 2. This predetermined range is calculated based on the decrease period (CATNOxIL) of the output value of the NOx sensor 30 and the recovery period (CATNOxIH) of the output value of the NOx sensor 30 calculated by the ECU 40.

The ECU 40 diagnoses that the NOx sensor 30 is abnormal when the difference between the recovery period (RETNOxIH) and the decrease period (RETNOx1L) of the output value of the NOx sensor 30 is shifted from the predetermined range, as shown in a latter half of FIG. 2.

(3) Amount of Correction of the Output Value of the NOx Sensor 30

The ECU 40 diagnoses whether the NOx sensor 30 is abnormal based on a correction amount to correct the output characteristics of the NOx sensor 30 by a correcting means to be described in greater detail hereinafter.

The ECU 40 diagnoses that the NOx sensor 30 is normal, if the correction amount by the correcting means is within a predetermined range. If the correction amount by the correcting means is shifted from the predetermined range, the ECU 40 diagnoses that the NOx sensor 30 is abnormal.

(Correcting Means)

The ECU 40 corrects the output characteristics of the NOx sensor 30 based on the output value of the NOx sensor 30 that varies by changing the spray characteristics for the specific cylinder.

For example, the ECU 40 changes the fuel injection quantity of the cylinder #1 alternately between QFINA and QFINB at every injection. The ECU 40 calculates the concentration of NOx discharged from the engine 2 when the fuel injection quantities are QFINA and QFINB based on the fuel injection quantities QFINA and QFINB. In an initial state before the NOx sensor 30 deteriorates or breaks down, a NOx concentration calculated based on the fuel injection quantities QFINA, QFINB generally accords with a NOx concentration calculated from initial output characteristics based on the output value of the NOx sensor 30.

Figure 3:
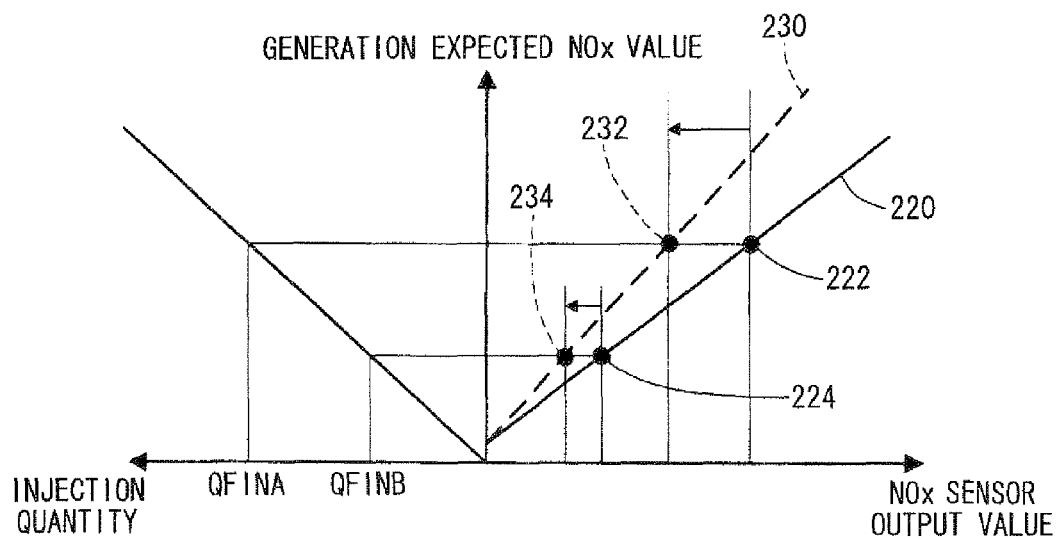
FIG. 3 is a characteristic diagram illustrating change of output characteristics of a NOx sensor according to the embodiment.

Accordingly, the ECU 40 calculates differences between the output values 232, 234 (FIG. 3) of the NOx sensor 30 detected when the fuel injection quantity is changed into QFINA and QFINB, and expected output values 222, 224 (FIG. 3) of the NOx sensor 30 calculated from initial output characteristics 220 of the NOx sensor 30 according to the NOx concentration at the fuel injection quantities QFINA, QFINB. Based on the differences, the ECU 40 calculates a correction amount to correct the initial output characteristics 220 and to obtain the present output characteristics 230 of the NOx sensor 30. The correction amount in this case is a slope of the output characteristics of the NOx sensor 30.

(Abnormality Diagnosis Routine)

Figure 4:
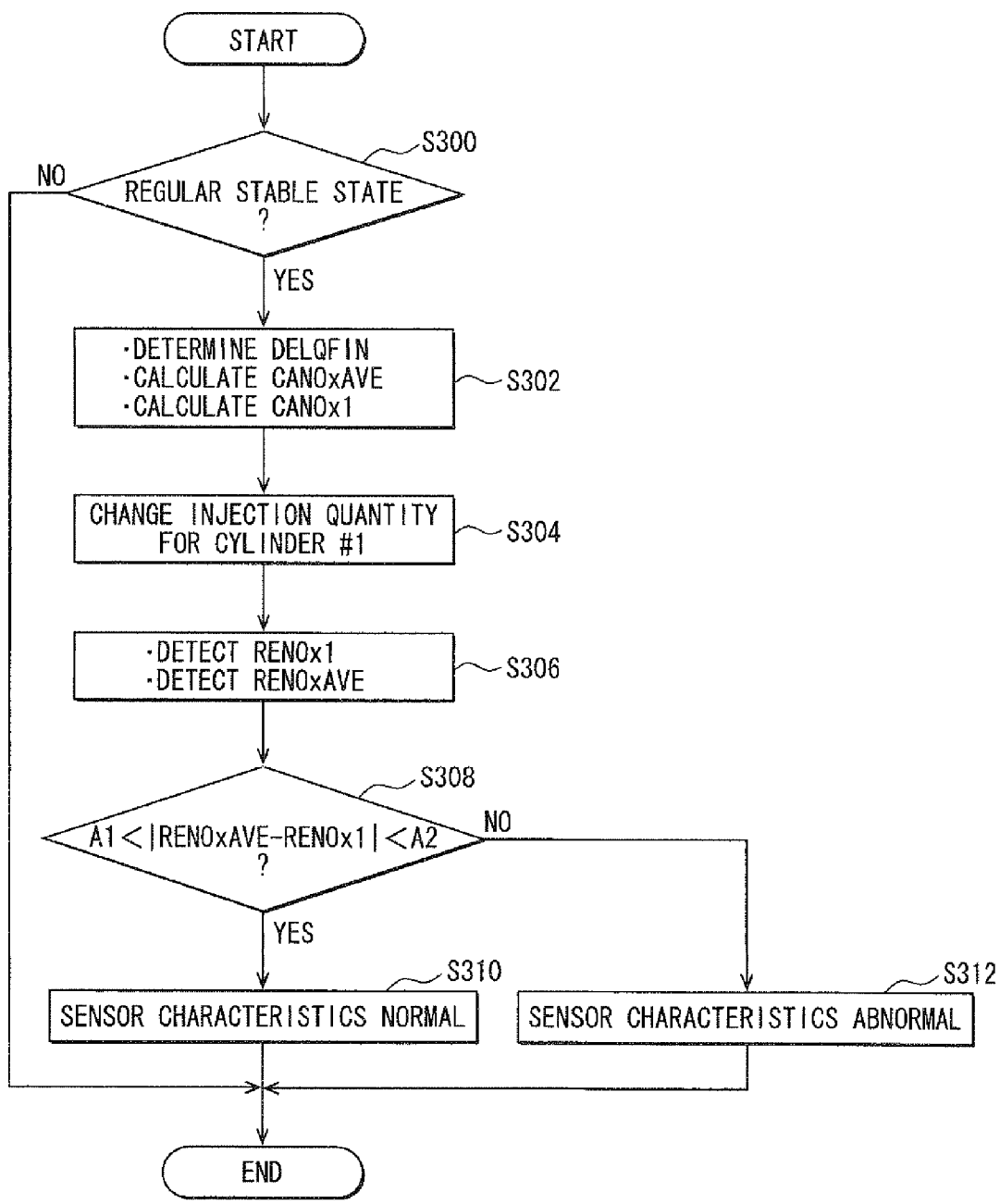
FIG. 4 is a flow chart illustrating abnormality diagnosis of the NOx sensor according to the embodiment.
Figure 5:
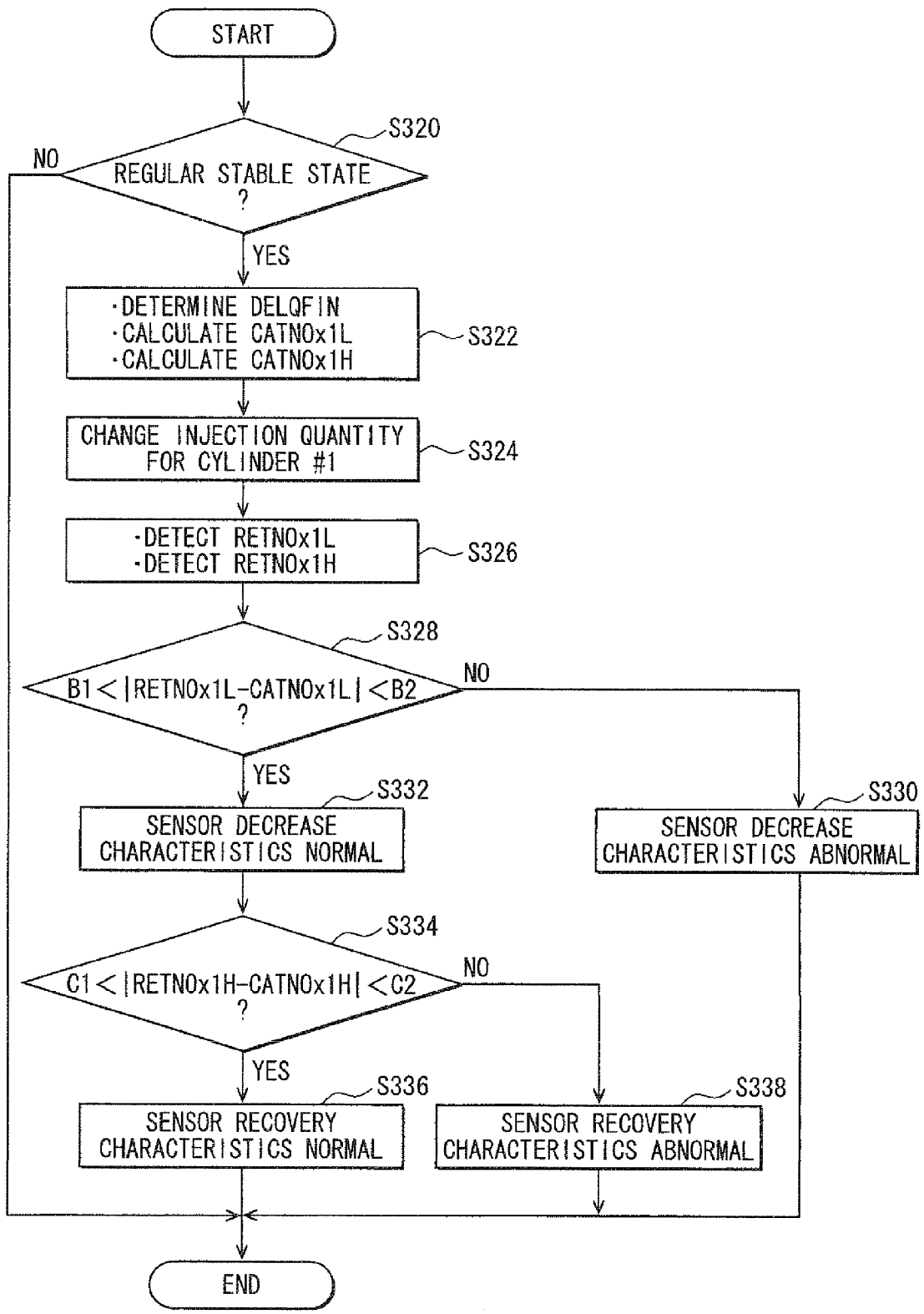
FIG. 5 is a flow chart illustrating another abnormality diagnosis of the NOx sensor according to the embodiment.
Figure 6:
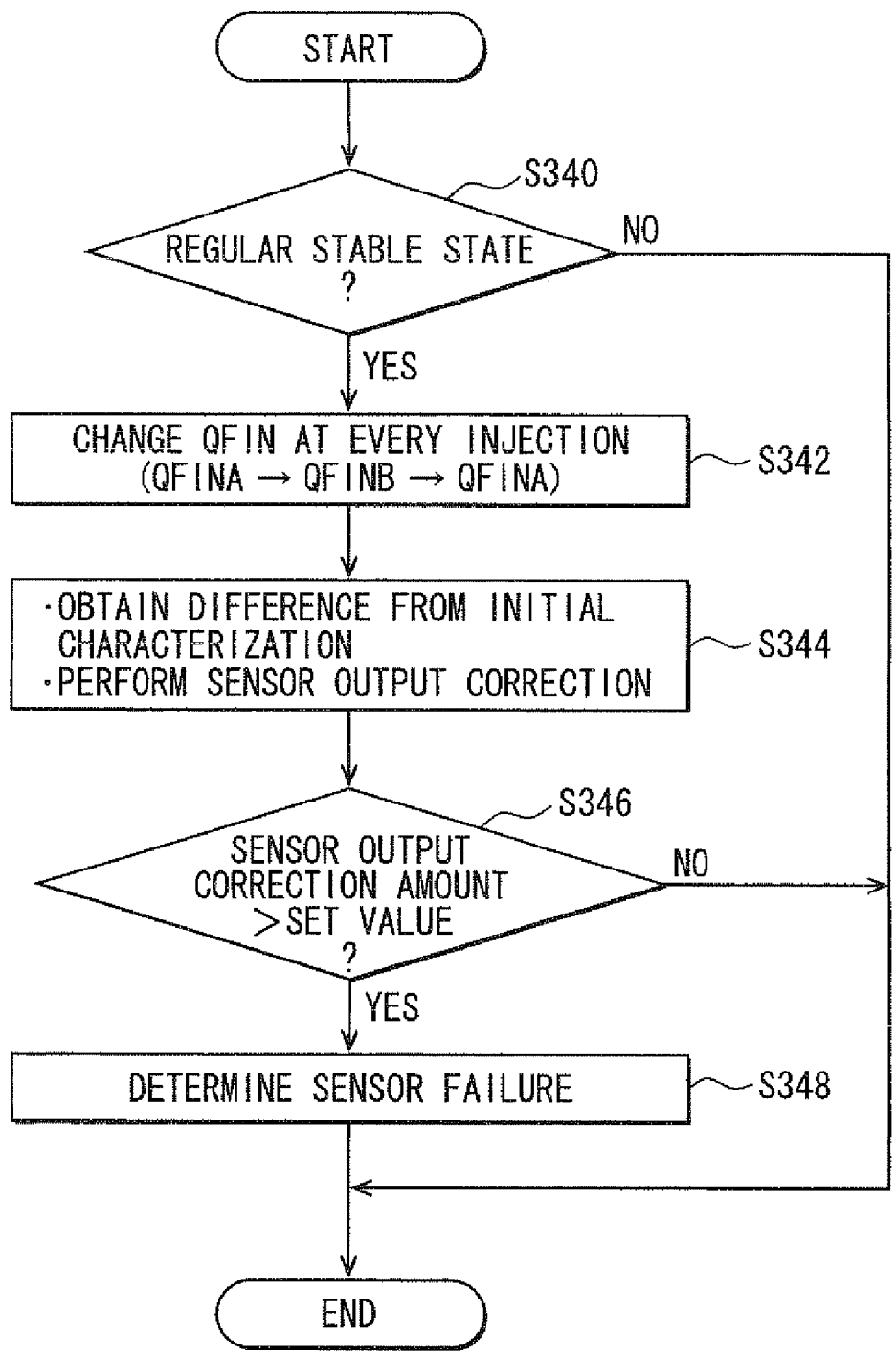
FIG. 6 is a flow chart illustrating yet another abnormality diagnosis of the NOx sensor according to the embodiment.

Diagnostic routines for diagnosing the abnormality of the NOx sensor 30 based on the variation of the output value of the NOx sensor 30 in the exhaust gas purifying system 10 in FIG. 4 to FIG. 6 are described. The routines of FIG. 4 to FIG. 6 are constantly performed. In FIG. 4 to FIG. 6, "S" expresses a step. The routines in FIG. 4 to FIG. 6 are stored in the storage device such as the ROM or flash memory of the ECU 40. In addition, at least one of the following routines in FIG. 4 to FIG. 6 may be performed.

(Variation of the Output Value of the NOx Sensor 30)

In the abnormality diagnosis routine of FIG. 4, the ECU 40 first determines whether the engine operation condition is in a regular stable state (S300). If the engine operation condition is not in a regular stable state (S300: No), the ECU 40 ends the present routine.

If the engine operation condition is in a regular stable state (S300: Yes), the ECU 40 calculates, as described above, the change injection quantity (DELQFIN) for the cylinder #1, the average value (CANOxAVE) of the NOx concentration in a regular stable state, and the concentration of NOx (CANOx1) discharged from the cylinder #1 as a result of subtracting the change injection quantity (DELQFIN) based on the engine operation condition, at S302.

At S304, the ECU 40 reduces the injection quantity of the fuel injection valve 4 for the cylinder #1 by the change injection quantity (DELQFIN). At S306, the ECU 40 detects the average value (RENOxAVE) of the concentration of NOx discharged from the engine 2 before changing the injection quantity command value by the change injection quantity (DELQFIN), and the minimum valve (RENOx1) of the NOx concentration that has been reduced as a result of changing the injection quantity command value from the target injection quantity command value by the change injection quantity (DELQFIN), from the output value of the NOx sensor 30.

Then, whether a difference |RENOxAVE−RENOx1| between the average value (RENOxAVE) of NOx concentration and the minimum valve (RENOx1) of NOx concentration satisfies the following equation (1) is determined (S308).

$$A1 < |RENOxAVE - RENOx1| < A2 \qquad (1)$$

Constants A1, A2 in the equation (1) express a range which can be covered when the NOx sensor 30 is normal based on the average value (CANOxAVE) of NOx concentration and the NOx concentration (CANOx1) after subtracting the change injection quantity (DELQFIN) calculated at S302.

If |RENOxAVE−RENOx1| satisfies the equation (1) (S308: Yes), the ECU 40 diagnoses that the NOx sensor 30 is normal (S310). If |RENOxAVE−RENOx1| does not satisfy the equation (1) (S308: No), the ECU 40 diagnoses that the NOx sensor 30 is abnormal.

(Response Time of the Output Value of the NOx Sensor 30)

In the abnormality diagnosis routine of FIG. 5, the ECU 40 first determines whether the engine operation condition is in a regular stable state (S320). If the engine operation condition is not in a regular stable state (S320: No), the ECU 40 ends the present routine.

If the engine operation condition is in a regular stable state (S320: Yes), the ECU 40 calculates at S322 the change injection quantity (DELQFIN) for the cylinder #1, the decrease period (CATNOxIL) of the output value of the NOx sensor 30, and the recovery period (CATNOxIH) of the output value of the NOx sensor 30, as described above, based on the initial output characteristics associated with the engine operation condition and the response time of the NOx sensor 30.

At S324, the ECU 40 decreases the injection quantity of the fuel injection valve 4 for the cylinder #1 by the change injection quantity (DELQFIN). At S326, the ECU 40 detects the actual decrease period (RETNOx1L) of the output value of the NOx sensor 30 and the actual recovery period (RETNOxIH) of the output value of the NOx sensor 30 as described above, from the output value of the NOx sensor 30.

Then, the ECU 40 determines whether a difference |RETNOx1L−CATNOx1L| between the detected decrease period (RETNOx1L) and the calculated decrease period (CATNOx1L) satisfies the following equation (2) (S328).

$$B1 < |RETNOx1L - CATNOx1L| < B-2 \qquad (2)$$

Constants B1, B2 in the equation (2) express a range that can be covered when the NOx sensor 30 is normal based on the decrease period (CATNOx1L) calculated at S322.

If |RETNOx1L−CATNOx1L| does not satisfy the equation (2) (S328: No), the ECU 40 diagnoses that characteristics of the decrease of the NOx sensor 30 are abnormal (S330), and ends the present routine.

If |RETNOx1L−CATNOx1L| satisfies the equation (2) (S328: Yes), the ECU 40 diagnoses that characteristics of the decrease of the NOx sensor 30 are normal (S332), and proceeds to processing at S334.

At S334, the ECU 40 determines whether a difference |RETNOx1H−CATNOx1H| between the detected recovery period (RETNOx1H) and the calculated recovery period (CATNOx1H) satisfies the following equation (3).

$$C1 < |RETNOx1H - CATNOx1H| < C2 \qquad (3)$$

Constants C1, C2 in the equation (3) express a range which can be covered when the NOx sensor 30 is normal based on the recovery period (CATNOx1H) calculated at S332.

If |RETNOx1H−CATNOx1H| satisfies the equation (3) (S334: Yes), the ECU 40 diagnoses that characteristics of the recovery of the NOx sensor 30 are normal (S336), and ends the present routine.

If |RETNOx1H−CATNOx1H| does not satisfy the equation (3) (S334: No), the ECU 40 diagnoses that characteristics of the recovery of the NOx sensor 30 are abnormal (S338), and ends the present routine.

(Correction Amount of the NOx Sensor 30)

In the correction routine of FIG. 6, the ECU 40 first determines whether the engine operation condition is in a regular stable state (S340). If the engine operation condition is not in a regular stable state (S340: No), the ECU 40 ends the present routine.

If the engine operation condition is in a regular stable state (S340: Yes), the ECU 40 changes an injection quantity QFIN of the cylinder #1, which is a specific cylinder, alternately between QFINA and QFINB at every injection, at S342.

At S344, the ECU 40 calculates the correction amount for correcting the slope of the initial output characteristics 220 based on a difference between the obtained output values of the NOx sensor 30 varying with the change of the injection quantity QFIN, and the expected output values of the NOx sensor 30 obtained from the initial output characteristics 220 (see FIG. 3) corresponding to QFINA and QFINB.

At S346, the ECU 40 determines whether the correction amount calculated at S346 is larger than a predetermined set value. If the correction amount calculated at S346 is equal to or smaller than the predetermined set value (S346: No), the ECU 40 diagnoses that the output characteristics of the NOx sensor 30 are normal, and ends the present routine.

If the correction amount calculated at S346 is larger than the predetermined set value (S346: Yes), the ECU 40 diagnoses that the output characteristics of the NOx sensor 30 are abnormal (S348), and ends the present routine.

Accordingly, the output characteristics of the NOx sensor are corrected if the correction amount is within a predetermined range, and it is diagnosed that the NOx sensor is abnormal when the correction amount is out of a predetermined normal range.

In the embodiment described above, the abnormality of the NOx sensor 30 is diagnosed based on the output value of the NOx sensor 30 varying with the change of the spray characteristics of the cylinder #1 which is a specific cylinder of the engine 2. Accordingly, the change of the engine operation condition is reduced as much as possible, and the abnormality of the NOx sensor is diagnosed with high precision.

In addition, if the change of the engine operation condition is somewhat allowable, the spray characteristics, not only for a single cylinder but for more than one specific cylinder (not all the cylinders) of all the cylinders, may be changed simultaneously.

(Other Embodiments)

In the above embodiment, the abnormality diagnosis of the NOx sensor 30 disposed on the upstream side of the NOx catalyst 12 is described. On the other hand, the abnormality diagnosis of the NOx sensor 32 disposed on the downstream side of the NOx catalyst 12 is performed when NOx is not reduced in the NOx catalyst 12, such as at low exhaust gas temperature at which the urea water is not hydrolyzed, or when addition of the urea water from the urea addition valve 14 is forcibly stopped.

The NOx removal system is not limited to the configuration that adds reducing agents such as urea water and reduces by a NOx catalyst. For example, the system may have a configuration that adsorbs NOx to an adsorbent and reduces adsorbed NOx by fuel in exhaust air.

In the above embodiment, the abnormality of the NOx sensor 30 is diagnosed based on the variation of the output value, the response time, or the correction amount of the NOx sensor 30 when the injection quantity of the fuel injection valve 4 of the cylinder #1, which is a specific cylinder, is changed. Alternatively, the abnormality of the NOx sensor 30 may be diagnosed, based on the variation of the output value, the response time, or the correction amount of the NOx sensor 30 when other spray characteristics of the fuel injection valve 4 of the cylinder #1, such as an injection timing and injection pattern, are changed.

In the above embodiment, the abnormality of the NOx sensor 30 is diagnosed when the engine operation condition is in a regular stable state where the engine rotational speed and fuel injection quantity are constant. Alternatively, as long as the concentration of NOx discharged from the engine 2 is calculated from the engine operation condition, the abnormality of the NOx sensor 30 may be diagnosed, for example, in a decelerating operation state.

In the above embodiment, the control programs stored in the storage device such as the ROM or flash memory of the ECU 40 make the ECU 40 serve as the operational state obtaining means, the output value obtaining means, the spray characteristics changing means, the diagnostic means, and the correcting means. Alternatively, a function of at least a part of these means may be configured by circuit logic of the ECU 40.

The NOx sensor diagnostic device of the invention may be applied also to an exhaust gas purifying system for internal combustion engines (e.g., gasoline engine) other than a diesel engine as long as they combust fuel to discharge NOx.

In addition, each function of the means that the invention includes is realized by hardware resources whose functions are specified by their configurations themselves, hardware resources whose functions are specified by programs, or their combinations. Furthermore, each function of these means is not limited to what is realized by hardware resources that are physically mutually independent of each other.

In this manner, the invention is not limited to the above embodiments, and may be applied to various embodiments without departing from the scope of the invention.

Additional advantages and modifications will readily occur to those skilled in the art. The invention in its broader terms is therefore not limited to the specific details, representative apparatus, and illustrative examples shown and described.

What is claimed is:

1. An NOx sensor diagnostic device for an internal combustion engine, comprising:
   an NOx sensor disposed in an exhaust passage of the engine;
   an output value obtaining means for obtaining an output value of the NOx sensor;
   a spray characteristics changing means for changing spray characteristics for a specific cylinder of a plurality of cylinders of the engine; and
   a diagnostic means for diagnosing abnormality of the NOx sensor, based on the output value of the NOx sensor that is changed as a result of the change of the spray characteristics for the specific cylinder by the spray characteristics changing means, wherein:

the diagnostic means diagnoses the abnormality of the NOx sensor based also on a response time for the change of the output value of the NOx sensor in response to the change of the spray characteristics for the specific cylinder; and the response time is one of:
- a decrease response time from a start of the change of the spray characteristics for the specific cylinder to a start of the change of the output value of the NOx sensor; and
- a recovery response time from an end of the change of the spray characteristics for the specific cylinder to an end of the change of the output value of the NOx sensor.

2. The NOx sensor diagnostic device according to claim 1, wherein the diagnostic means diagnoses the abnormality of the NOx sensor based on an amount of the change of the output value of the NOx sensor.

3. The NOx sensor diagnostic device according to claim 1, further comprising a correcting means for correcting output characteristics of the NOx sensor based on the output value of the NOx sensor that is changed as a result of the change of the spray characteristics for the specific cylinder, wherein the diagnostic means diagnoses the abnormality of the NOx sensor based on an amount of the correction by the correcting means.

4. An exhaust gas purifying system for an internal combustion engine, comprising:

a NOx removal system disposed in an exhaust passage of the engine;

a NOx sensor disposed in the exhaust passage at least on an upstream side of the NOx removal system in a flow direction of exhaust air flowing through the exhaust passage; and the NOx sensor diagnostic device recited in claim 1.

5. A method comprising:

obtaining an output value of an NOx sensor disposed in an exhaust passage of an internal combustion engine;

changing spray characteristics for a specific cylinder of a plurality of cylinders of the engine; and diagnosing abnormality of the NOx sensor, based on the output value of the NOx sensor that is changed as a result of the change of the spray characteristics for the specific cylinder and also based on a response time for the change of the output value of the NOx sensor in response to the change of the spray characteristics for the specific cylinder; and the response time is one of:
- a decrease response time from a start of the change of the spray characteristics for the specific cylinder to a start of the change of the output value of the NOx sensor; and
- a recovery response time from an end of the change of the spray characteristics for the specific cylinder to an end of the change of the output value of the NOx sensor.

6. The method according to claim 5, wherein the abnormality of the NOx sensor is diagnosed based on an amount of the change of the output value of the NOx sensor.

7. The method according to claim 5, further comprising correcting output characteristics of the NOx sensor based on the output value of the NOx sensor that is changed as a result of the change of the spray characteristics for the specific cylinder, wherein the abnormality of the NOx sensor is based on an amount of the correction.

* * * * *